(12) United States Patent
Boddy et al.

(10) Patent No.: US 8,722,365 B2
(45) Date of Patent: May 13, 2014

(54) **METABOLICALLY ENGINEERED *ESCHERICHIA COLI* FOR ENHANCED PRODUCTION OF SIALIC ACID**

(75) Inventors: Christopher N. Boddy, Syracuse, NY (US); Benjamin R. Lundgren, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 1154 days.

(21) Appl. No.: 11/861,496

(22) Filed: Sep. 26, 2007

(65) Prior Publication Data
US 2008/0153133 A1    Jun. 26, 2008

Related U.S. Application Data (60) Provisional application No. 60/826,919, filed on Sep. 26, 2006.

(51) Int. Cl.
| | | |
|---|---|---|
| *C12P 19/26* | (2006.01) | |
| *C12Q 1/68* | (2006.01) | |
| *C12P 21/06* | (2006.01) | |
| *C12N 15/00* | (2006.01) | |
| *C12N 1/20* | (2006.01) | |
| *C12N 9/00* | (2006.01) | |
| *C12N 9/10* | (2006.01) | |
| *C12N 15/74* | (2006.01) | |
| *C07K 1/00* | (2006.01) | |
| *C07H 21/04* | (2006.01) | |
| *C07H 21/02* | (2006.01) | |

(52) U.S. Cl.
USPC ........... 435/84; 435/6.17; 435/69.1; 435/183; 435/193; 435/320.1; 435/252.3; 435/252.33; 435/471; 530/350; 536/23.1; 536/23.2

(58) Field of Classification Search
None
See application file for complete search history.

(56) References Cited

FOREIGN PATENT DOCUMENTS

WO    WO2008/040717 A2    4/2008

OTHER PUBLICATIONS

Whisstock et al. Quaterly Reviews of Biophysics, 2003, "Prediction of protein function from protein sequence and structure", 36(3): 307-340.*

Lundgren, et al., "Sialic acid overproduction by metabolic engineering of *Escherichia coli*", 24th Annual Graduate Student Symposium, May 18, 2006, retrieved from the internet, URL:http://wings.buffalo.edu/chem-gss/2006_abstracts.pdf.

Tammer, M. E., "The enzymes of sialic acid biosynthesis", Biorganic Chemistry, Academic Press Inc., New York, NY, vol. 33, No. 3, Jun. 1, 2005, pp. 216-228.

Plumbridge, et al., "Coordinated regulation of amino sugar-synthesizing and -degrading enzymes in *Escherichia coli* K-12", Journal of Bacteriology, vol. 175, No. 16, 1993, pp. 4951-4956.

Deng, et al., "Engineering a new pathway for N-acetylglucosamine production: Coupling a catabolic enzyme, glucosamine-6 phosphate deaminase, with a biosynthetic enzyme, glocosamine-6-phosphate N-acetyltransferase" Enzyme and Microbial Technology, Stoneham, MA, vol. 39, No. 4, Aug. 2, 2006, pp. 828-834.

Lundgren, et al., "Sialic acid and N-acyl sialic acid analog production by fermentation of metabolically and genetically engineered *Escherichia coli*", Organic & Biomolecular Chemistry, Jun. 21, 2007, vol. 5, No. 12, pp. 1903-1909.

* cited by examiner

*Primary Examiner* — Iqbal H Chowdhury
(74) *Attorney, Agent, or Firm* — David L. Nocilly; Frederick J. M. Price; Bond Schoneck & King, PLLC (57) ABSTRACT

A metabolically engineered *E. coli* strain which produces sialic acid and a method of making said strain. In the engineered *E. coli* cells, the nanT (sialic acid transporter) and nanA (sialic acid adolase) genes are inactivated, and the neuC and neuB genes of sialic acid biosynthesis in *Neisseria meningitidis* group B are introduced and overexpressed in the nanT⁻ nanA⁻ *E. coli* cell. In addition, the glucosamine synthase gene, glmS, of *E. coli* is co-overexpressed with neuB and neuC.

6 Claims, 5 Drawing Sheets

SEQUENCE LISTING

<160> NUMBER OF SEQ ID NOS: 12

<210> SEQ ID NO 1
<211> LENGTH: 36
<212> TYPE: DNA
<213> ORGANISM: Neisseria meningitidis

<400> SEQUENCE: 1

```
cgcacatatg caaaacaaca acgaatttaa aattgg                                      36

<210> SEQ ID NO 2
<211> LENGTH: 41
<212> TYPE: DNA
<213> ORGANISM: Neisseria meningitidis

<400> SEQUENCE: 2
cagcgaattc ttattcaata tcagtttttt tgatttgagc a                                41

<210> SEQ ID NO 3
<211> LENGTH: 37
<212> TYPE: DNA
<213> ORGANISM: Neisseria meningitidis

<400> SEQUENCE: 3
cgcagctagc aaaaggattc tttgcattac aggtacc                                    37

<210> SEQ ID NO 4
<211> LENGTH: 33
<212> TYPE: DNA
<213> ORGANISM: Neisseria meningitidis

<400> SEQUENCE: 4
cagcgaattc ctagtcataa ctggtggtac att                                        33

<210> SEQ ID NO 5
<211> LENGTH: 75
<212> TYPE: DNA
<213> ORGANISM: Artificial Sequence
<220> FEATURE:
<223> OTHER INFORMATION: Plasmid pBR322

<400> SEQUENCE: 5
atggcaacga atttacgtgg cgtaatggct gcactcctga ctccttttga tcatgtttga           60
cagcttatca tcgat                                                            75

<210> SEQ ID NO 6
<211> LENGTH: 75
<212> TYPE: DNA
<213> ORGANISM: Artificial Sequence
<220> FEATURE:
<223> OTHER INFORMATION: Plasmid pBR322

<400> SEQUENCE: 6
tcacccgcgc tcttgcatca actgctgggc cagcgccttc agttctggca tccaattctt           60
ggagtggtga atccg                                                            75

<210> SEQ ID NO 7
<211> LENGTH: 24
<212> TYPE: DNA
<213> ORGANISM: XL1 Blue Escherichia coli

<400> SEQUENCE: 7
gacgcatatg ggcatcgccc accg                                                  24

<210> SEQ ID NO 8
<211> LENGTH: 30
<212> TYPE: DNA
<213> ORGANISM: XL1 Blue Escherichia coli

<400> SEQUENCE: 8
gacgttaact tttggttttg actaaatcgt                                            30
```

```
<210> SEQ ID NO 9
<211> LENGTH: 28
<212> TYPE: DNA
<213> ORGANISM: XL1 Blue Escherichia coli

<400> SEQUENCE: 9
gcgccatatg tgtggaattg ttggcgcg                                          28

<210> SEQ ID NO 10
<211> LENGTH: 34
<212> TYPE: DNA
<213> ORGANISM: XL1 Blue Escherichia coli

<400> SEQUENCE: 10
gcgcgaattc ttactcaacc gtaaccgatt ttgc                                   34

<210> SEQ ID NO 11
<211> LENGTH: 70
<212> TYPE: DNA
<213> ORGANISM: Artificial Sequence
<220> FEATURE:
<223> OTHER INFORMATION: Plasmid pKD3

<400> SEQUENCE: 11
atgtatgcat taacccaggg ccggatcttt accggccacg aatttcttga gtgtaggctg       60
gagctgcttc                                                              70

<210> SEQ ID NO 12
<211> LENGTH: 70
<212> TYPE: DNA
<213> ORGANISM: Artificial Sequence
<220> FEATURE:
<223> OTHER INFORMATION: Plasmid pKD3

<400> SEQUENCE: 12
ttattgagtt acgacctcgt taccgttaac gatgctcttg gtgattttaa catatgaata       60
tcctccttag                                                              70
```

METABOLICALLY ENGINEERED ESCHERICHIA COLI FOR ENHANCED PRODUCTION OF SIALIC ACID

CROSS-REFERENCE TO RELATED APPLICATION

The present application claims priority to U.S. Provisional Application No. 60/826,919, filed Sep. 26, 2006.

BACKGROUND OF THE INVENTION

1. Field of Invention

The present invention relates to metabolically engineered Escherichia coli ("E. coli"), and, more specifically, to metabolically engineered E. coli for enhanced production of sialic acid.

2. Description of Prior Art

Sialic acid is a biologically complex carbohydrate that plays important roles in cell signaling, bacterial pathogenesis and tumour metastasis. The physiochemical properties of sialic acid have made it a valuable resource with an increasing demand in both medicine and biotechnology.

Figure 1:
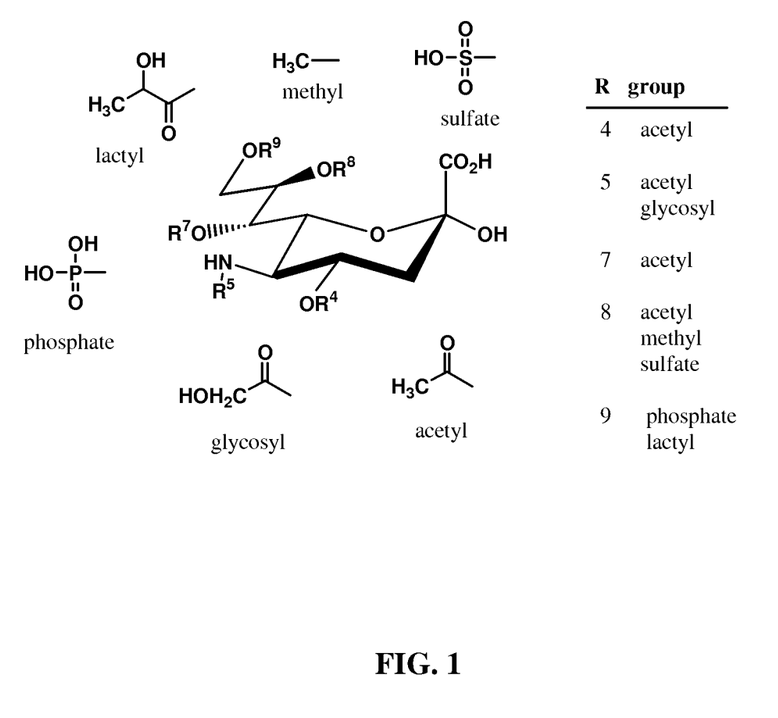
FIG. 1 is a high level schematic illustrating the diversity of the sialic acid family.

More precisely, sialic acid is a general term used to describe a large family of acidic sugars that are predominantly found on the cell surface of eukaryotic cells. The most common sialic acid is N-acetylneuraminic acid or Neu5Ac, an acidic nine-carbon sugar that undergoes several modifications to generate the members of the sialic acid family. As seen in FIG. 1, the diversity of the sialic acid family is represented with over 50 known members. Sialic acid represents a large family of cell-surface carbohydrates that are derived from an acidic, nine-carbon parent compound called N-acetylneuraminic acid or Neu5Ac. Neu5Ac is often decorated with acetyl, phosphate, methyl, sulfate and lactyl groups, which are required for desirable cell signaling and cell adhesion events mediated by sialic acid.

Sialic acid performs a diverse array of functions including important biological processes such as glycoprotein stability, cellular immunity, solute transport, self-recognition, neuronal plasticity and cell signaling. Sialic acid also has a significant role in human disease. For example, cancerous cells have been shown to have elevated sialic acid levels or sialylation on their surfaces. Excess sialylation has been shown to promote invasiveness and reduce intercellular interactions, which are features of tumour metastasis. Sialic acid is currently being researched as a tool for the non-invasive imaging of cancer tissue in vivo. Increased levels of sialic acid have been observed for cardiovascular disease, alcoholism and diabetes, thus making sialic acid a marker for diagnosing and detecting such deadly diseases. Some bacterial pathogens possess a polysialic acid capsule that serves as a masking agent by mimicking the extracellular surface of mammalian cells. Polysialic acid capsules protect the underlying bacteria from the host immune response, which allows the bacteria to establish an infection. Polysialic acid capsulated bacteria are leading causative agents of meningitis, a life threatening disease in adults and children. Lastly, analogs of sialic acid have found important roles in the pharmaceutical industry as influenza neuraminidase inhibitors, e.g., Relenza®, stabilizers of therapeutics and diagnostic agents.

The resource availability of sialic acid is limited and costly. Traditionally, sialic acid has been isolated from egg yolk, milk whey and edible bird nest, which requires a lengthy, cumbersome purification process. The overall yields are typically low (~10-20%) and the purity is marginal. Synthetic routes in sialic acid chemistry are challenging, because of the target molecule's complexity. To circumvent the difficulties associated with sialic acid isolation, purification and synthetic chemistry, enzymatic synthesis is currently the preferred method for sialic acid production. The cloning and subsequent isolation of enzymes involved in the biosynthesis and degradation of sialic acid has enabled researchers to produce sialic acid in vitro by a straightforward enzymatic reaction. Enzymatic synthesis of sialic acid has a high yield (80%) and generates a pure product through a direct crystallization of the enzymatic mixture. The major drawbacks of enzymatic synthesis in sialic acid production are its cost and scalability at the industrial level.

The methods for producing sialic acid, discussed supra, are insufficient in meeting the large demand of the medical and biotechnological industries. A metabolic engineering approach that successfully overcomes the problems associated with, e.g. sialic acid isolation, purification, synthetic chemistry, production yield, cost, and scalability at the industrial level, would represent a significant and long awaited advance in the field.

OBJECTS AND ADVANTAGES

In order to resolve the aforementioned problems associated with the production of sialic acid, it is a principal object and advantage of the present invention to provide a metabolically engineered E. coli cell, wherein said cell produces sialic acid.

It is an additional object and advantage of the present invention to provide a method for making a metabolically engineered E. coli cell, wherein said cell produces sialic acid.

It is a further object and advantage of the present invention to provide a method for making sialic acid through the use of a metabolically engineered E. coli cell.

Other objects and advantages of the present invention will in part be obvious, and in part appear hereinafter.

SUMMARY OF THE INVENTION

In accordance with an embodiment of the present invention, a metabolically engineered E. coli cell which produces sialic acid and a method of making said cell are provided. Specifically, a metabolically engineered E. coli cell is provided wherein nanT (sialic acid transporter) and nanA (sialic acid adolase) genes have been inactivated, neuC and neuB genes of sialic acid bioysnthesis in Neisseria meningitidis group B have been introduced and overexpressed into the nanT− nanA− E. coli cell, and the glucosamine synthase gene, glmS, of E. coli has been co-overexpressed with neuB and neuC. In accordance with a further embodiment of the present invention, a method of making sialic acid through the use of said metabolically engineered E. coli cell is provided.

The present invention provides a genetically engineered microbe, comprising: an inactivating mutation in a first DNA molecule in the microbe, wherein the first DNA molecule encodes a sialic acid transporter; an inactivating mutation in a second DNA molecule in the microbe, wherein the second DNA molecule encodes a sialic acid aldolase; and a first enzyme-encoding recombinant DNA molecule, wherein the first enzyme-encoding recombinant DNA molecule encodes an enzyme selected from the group consisting of a sialic acid synthase and a UDP-N-acetylglucosamine 2-epimerase.

In some embodiments of the present invention, the microbe further comprises a second enzyme-encoding recombinant DNA molecule, wherein the second enzyme-encoding recombinant DNA molecule encodes an enzyme selected from the group consisting of a sialic acid synthase and a UDP-N-acetylglucosamine 2-epimerase. Preferably, the microbe further comprises a recombinant DNA molecule or a mutation in a DNA molecule in the g/m or nag pathway that provides increased UDP-GlcNAc levels compared with a wild-type strain. In some embodiments of the present invention, the microbe further comprises a recombinant DNA molecule encoding a glucosamine synthase. Preferably, the recombinant DNA molecule encoding a glucosamine synthase is a glmS gene.

In some embodiments of the present invention, the microbe is E. coli. Preferably, the inactivating mutations in the microbe are in the nanT and nanA genes. In further embodiments of the present invention, the first and second enzyme-encoding recombinant DNA molecules are the neuC and neuB genes. Preferably, the neuC and neuB genes originate from Neisseria meningitidis. Preferably, the microbes of the present invention are capable of transporting sialic acid out of the cell.

The present invention also provides a method of forming a genetically engineered microbe for producing sialic acid, comprising the steps of: introducing an inactivating mutation into a first DNA molecule encoding a sialic acid transporter in the microbe; introducing an inactivating mutation into a second DNA molecule encoding a sialic acid aldolase in the microbe; and introducing a first enzyme-encoding recombinant DNA molecule in the microbe, wherein said first enzyme-encoding recombinant DNA molecule encodes an enzyme selected from the group consisting of a sialic acid synthase and a UDP-N-acetylglucosamine 2-epimerase.

In some embodiments of the present invention, the method of forming a genetically engineered microbe for producing sialic acid further comprises the step of introducing a second enzyme-encoding recombinant DNA molecule, wherein the second enzyme-encoding recombinant DNA molecule encodes an enzyme selected from the group consisting of a sialic acid synthase and a UDP-N-acetylglucosamine 2-epimerase. Preferably, methods of the present invention further comprise the step of introducing a recombinant DNA molecule or a mutation in a DNA molecule in the g/m or nag pathway that provides increased UDP-GlcNAc levels compared with a wild-type strain. Some methods of the present invention further comprise the step of introducing a recombinant DNA molecule encoding a glucosamine synthase into the microbe.

The present invention further provides a method of producing sialic acid, comprising the steps of: providing a genetically engineered microbe, wherein the microbe comprises an inactivating mutation in a first DNA molecule in the microbe that encodes a sialic acid transporter; an inactivating mutation in a second DNA molecule in the microbe the encodes a sialic acid aldolase; and a first enzyme-encoding recombinant DNA molecule in the microbe, wherein the first enzyme-encoding recombinant DNA molecule encodes an enzyme selected from the group consisting of a sialic acid synthase and a UDP-N-acetylglucosamine 2-epimerase; and culturing the microbe in the presence of a carbon source.

In some embodiments of the present invention, the carbon source can be, but is not limited to, glucose, glycerol, fructose, or N-acetylglucosamine.

The present invention further provides a genetically engineered microbe, comprising: an inactivating mutation in a DNA molecule in the microbe, wherein the DNA molecule encodes a sialic acid aldolase; a first enzyme-encoding recombinant DNA molecule, wherein the first enzyme-encoding recombinant DNA molecule encodes a sialic acid synthase; and a second enzyme-encoding recombinant DNA molecule, wherein the second enzyme-encoding recombinant DNA molecule encodes a UDP-N-acetylglucosamine 2-epimerase.

The present invention also provides a method of producing an N-acyl sialic acid analog, comprising the steps of: providing a genetically engineered microbe, wherein the microbe comprises an inactivating mutation in a first DNA molecule in the microbe that encodes a sialic acid transporter; an inactivating mutation in a second DNA molecule in the microbe that encodes a sialic acid aldolase; and a first enzyme-encoding recombinant DNA molecule in the microbe, wherein the first enzyme-encoding recombinant DNA molecule encodes an enzyme selected from the group consisting of a sialic acid synthase and a UDP-N-acetylglucosamine 2-epimerase; and culturing the microbe in the presence of a reagent such that intracellular UDP-N-acylglucosamine is generated. In some embodiments of the present invention, the reagent can be, but is not limited to, an N-acylglucosamine analog.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 2:
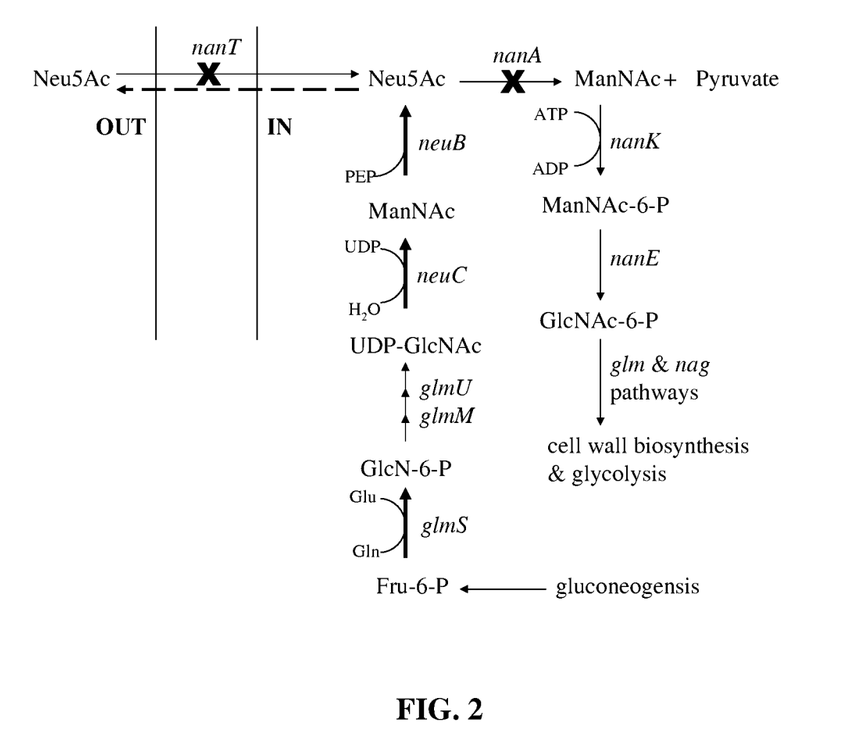
FIG. 2 is high level schematic illustrating the production of sialic acid by a metabolically engineered E. coli cell in accordance with an embodiment of the present invention.

Bacterial sialic acid metabolism is well understood, and both anabolic and catabolic pathways have been identified. The nan operon encodes the proteins necessary for sialic acid catabolism and is found across hundreds of bacterial species. In E. coli, this pathway consists of a sialic acid transporter, NanT, a sialic acid aldolase, NanA, a ManNAc kinase, NanK, and a ManNAc-6-phosphate epimerase, NanE, as seen in FIG. 2. NanT is not limited to its function in sialic acid catabolism, as it has also been demonstrated to be involved in the synthesis of polysialic acid capsules by mediating uptake of sialic acid and incorporation of the sialic acid into the polysialic acid capsule.

There is seen in FIG. 2 sialic acid production in metabolically engineered Escherichia coli. Crosses indicate blocks in pathways due to gene inactivation. Bold arrows indicate elevated fluxes of metabolism by gene overexpression. Sialic acid catabolism was blocked by the inactivation of the nanT (sialic acid transporter) and nanA (sialic acid aldolase) genes (crosses). The neuC and neuB genes of sialic acid biosynthesis in Neisseria meningitidis group B were introduced and overexpressed into the nanT$^-$ nanA$^-$ E. coli strain (bold arrows). Increase in the metabolic flux of UPD-GlcNAc, the substrate of the neuBC pathway, was achieved by engineering glmS overexpression into the pathway (bold arrows). The dotted line represents sialic acid efflux by an undefined mechanism. The abbreviations are as follows, Neu5Ac: N-acetylneuraminic acid, ManNAc: N-acetylmannosamine, ManNAc-6-P: N-acetylmannosamine-6-phosphate, GlcNAc-6-P: N-acetylglucosamine-6-phosphate, UDP-GlcNAc: uridine diphosphate N-acetylglucosamine, GlcN-6-P: glucosamine-6-phosphate, Fru-6-P: fructose-6-phosphate, PEP: phosphoenolpyruvate, Gln: glutamine, Glu: glutamate, UDP: uridine diphosphate, nanT: sialic acid transporter, nanA: sialic acid aldolase, nanK: ManNAc kinase, nanE: ManNAc-6-P epimerase, glmS: glucosamine synthase, gluM: glucosamine mutase, glmU: GlcNAc-1-P uridyltransferase/GlcN-1-P acetyltransferase, neuC: UDP-GlcNAc 2-epimerase, neuB: sialic acid synthase, glm: UDP-GlcNAc biosynthesis, nag: GlcNAc degradation. The products of the nan system are GlcNAc and pyruvate, which are key molecules in primary metabolism.

In contrast to sialic acid catabolism, bacterial sialic acid biosynthesis is limited to a subset of pathogenic bacteria, including E. coli K1 and N. meningitidis group B that synthesize a polysialic acid capsule. The two proteins that participate in the biosynthesis of sialic acid are NeuC and NeuB. NeuC is a hydrolyzing UDP-GlcNAc 2-epimerase that generates ManNAc. NeuB is a synthase that combines ManNAc and phosphoenolpyruvate to form sialic acid. Other proteins of the neu pathway incorporate sialic acid into the polysialic acid capsule. Two sialic acid biosynthetic pathways were engineered from enzymes of the nan and neu systems. The first engineered pathway involved the catabolic NanAEK proteins. Because NanA has been shown to synthesize sialic acid in the presence of excess pyruvate in vitro, it was hypothesized that the nanAEK pathway could be reversed by supplying excess GlcNAc to cultures of metabolically engineered E. coli cells. GlcNAc is readily taken up by E. coli cells, and it was expected that intracellular GlcNAc would be converted to ManNAc through the assistance of the NanEK proteins. The high intracellular concentration of ManNAc would then drive sialic acid synthesis through NanA catalysis. Sialic acid production was not observed from shake-flask experiments of BRL01 (a nanT$^-$ E. coli strain that possesses a lac-controlled T7 RNA polymerase gene)/nanAEK, and as a result, the nanAEK pathway was concluded as ineffective in sialic acid production.

The second engineered pathway focused on the NeuC and NeuB proteins of N. meningitidis group B, which will be discussed infra. A benefit of this pathway is the substrate specificity of NeuC, which converts a common bacterial metabolite, UDP-GlcNAc, into ManNAc, as seen in FIG. 2. NeuC, a hydrolyzing UDP-GlcNAc 2-epimerase, is also more efficient than certain other epimerases due to its ability to couple energy from a hydrolysis reaction to drive epimerization. Due to its energetic efficiency through its ability to use energy liberated from a first reaction to drive a subsequent reaction, UDP-GlcNAc 2-epimerase is preferred for sialic acid production in accordance with the present invention.

Figure 5:
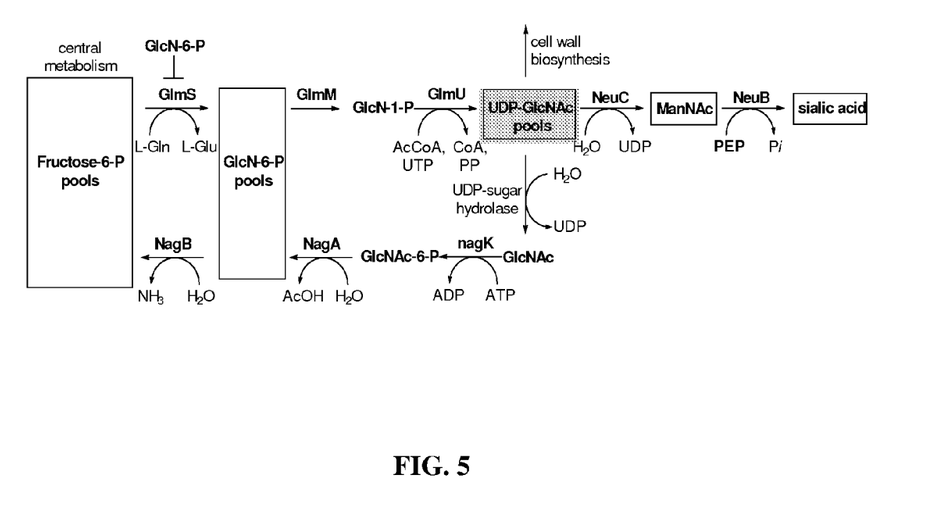
FIG. 5 is a schematic illustrating pathways involved in the production of sialic acid in accordance with an embodiment of the present invention.

As the direct substrate of the neuBC pathway, intracellular UDP-GlcNAc pools control the metabolic flux into the sialic acid synthetic pathway, controlling sialic acid titer. FIG. 5 shows pathways involved in the maintenance of the UPD-GlcNAc pools. Increasing UDP-GlcNAc pools increases sialic acid productivity and culture titer. UDP-GlcNAc is a key component of bacterial cell wall biosynthesis and is linked to central metabolism by the g/m pathway, which converts fructose-6-phosphate (Fru-6P) into UDP-GlcNAc, and the nag pathway, which returns hydrolyzed UDP-GlcNAc to Fru-6P. These two pathways energetically couple central bacterial metabolism to cell wall biosynthesis and sialic acid production. The present invention provides methods for enhancing flux through the g/m pathway and/or decreasing flux through the nag pathway to increase UDP-GlcNAc pools, thereby improving sialic acid productivity. Controlling the degree and direction of the cross talk between the key metabolic linchpin Fru-6P and UDP-GlcNAc will enable sialic acid productivity to be optimized. The control of the g/m and/or the nag pathways and the increase in UDP-GlcNAc levels compared to wild-type strains, as provided by the present invention, are essential to the efficient commercial production of sialic acid.

In accordance with an embodiment of the present invention, E. Coli has been successfully engineered to produce sialic acid, a complex, biologically important molecule that has significant applications in both medicine and biotechnology. The costs of sialic acid production from metabolically engineered E. coli is substantially lower than that of chemical synthesis, and unlike enzymatic synthesis, metabolically engineered E. coli are more readily scalable for industrial production.

From low-cell density shake-flask cultures, sialic acid production reached a maximum of 1.5 g l$^{-1}$. Incorporation of this metabolically engineered strain into high-cell density fermentation in accordance with the present invention will likely increase sialic acid production to several grams per liter. In fact, a ten-fold increase in sialic acid production is possible from a high-density cell culture, e.g., greater than 15 g l$^{-1}$. At an industrial level of production, the method of the present invention serves as a cost-effective resource for sialic acid, supplying enough sialic acid to meet the continually increasing demands of the medical, biotechnological and scientific communities.

In some embodiments of the present invention, sialic acid production may further be enhanced by modifying the preexisting engineered neuBCglmS pathway. For example, engineering a G/mS protein that has a higher turnover rate in glucosamine synthesis and is more cytosolic soluble may be performed.

Another key aspect of the present invention is the unexpected efflux of sialic acid from the cytosol to the media. Standard teachings in the art regarding transport of sugars across biological membranes suggest that acidic sugars cannot cross membranes. Their high level of hydrophilicity coupled with their negative charge renders them membrane impermeable. This is well documented for phosphorylated and sulfated sugars. Nonulosonic acids, such as sialic acid and its analogs, are acid sugars and as such the teachings in the art has indicated that these compounds will not be able to cross membranes. Thus, in accordance with the teachings in the art, if sialic acid is produced intracellularly, as occurs in the present invention, it will not be able to leave the cell and enter the media. This is not the case, however, for sialic acid produced in accordance with the present invention. The present invention provides microbes and methods for producing sialic acid where high levels of sialic acid can be produced in the cytosol and where the sialic acid does cross the membrane and enters the media. This membrane transport dramatically increase the productivity of the system since the producing cells do not have to die and lyse to release the sialic acid, but can rather release sialic acid and continue to produce more product. Thus, in preferred embodiments of the present invention, the microbes used to produce sialic acid are capable of transporting sialic acid out of the cell. As referred to herein, "transporting" is not limited to transporting by a protein mediated process, but encompasses movement of sialic acid across the cell membrane by any mechanism.

An extension of sialic acid production in metabolically engineered E. coli, in accordance with an embodiment of the present invention is in the biosynthesis and production of sialic acid analogs (unnatural sialic acids) in significant quantities. Sialic acid analogs are used as probes in cellular interactions, agents in visualizing cellular surfaces in vivo and as components in pharmaceuticals. Currently, sialic acid analogs are synthesized and engineered into cellular surfaces from expensive, derivatized mannosamine sugars. In contrast, sialic acid analog production from metabolically engineered *E. coli* in accordance with the present invention utilizes glucosamine derivatives, which are less expensive than their mannosamine equivalents. Downstream processes involving sialic acid analogs will be more effectively accomplished with direct access to the sialic acid analog rather than its mannosamine precursor. Therefore, sialic acid production from metabolically engineered *E. coli* in accordance with the present invention is a cost-effective and direct route for synthesizing sialic acid and its analogs, such as N-acyl sialic acid analogs. Examples of N-acyl sialic acid analogs include, but are not limited to, N-azidoacetyl-, N-levulinoyl-, and N-butanoyl sialic acid.

In some embodiments of the present invention, a method of producing an N-acyl sialic acid analog comprises the steps of: providing a genetically engineered microbe, wherein the microbe comprises an inactivating mutation in a first DNA molecule in the microbe that encodes a sialic acid transporter; an inactivating mutation in a second DNA molecule in the microbe the encodes sialic acid aldolase; and a first enzyme-encoding recombinant DNA molecule in the microbe, wherein the first enzyme-encoding recombinant DNA molecule encodes an enzyme selected from the group consisting of a sialic acid synthase and a UDP-N-acetylglucosamine 2-epimerase; and culturing the microbe in the presence of a reagent such that intracellular UDP-N-acylglucosamine is generated. Any suitable reagents may be used, such as any N-acylglucosamine carbon source. Preferably, the reagent is an N-acylglucosamine analog. An acyltransferase may also be used to facilitate the formation of a reagent or the generation of intracellular UDP-N-acylglucosamine.

Advantages of the present invention are illustrated by the following examples. However, the particular materials and amounts thereof recited in these examples, as well as other conditions and details, are to be interpreted to apply broadly in the art and should not be construed to unduly restrict or limit the invention in any way.

Example 1

This example relates to the deletion of a key *E. coli* gene, nanT, to generate a nanT⁻ *E. coli* mutant because nanT is a sialic acid transporter and is responsible for sialic acid uptake.

A nanT knockout *E. coli* K-12 strain MG1655 named FB21071 was requested from the Blattner laboratory at the University of Wisconsin, Madison, Wis. This strain has a Tn5 insertion into the nanT gene that confers kanamycin resistance. To allow for gene expression from T7lac-promoter plasmids, a T7 RNA polymerase gene under a lac-promoter was inserted into the chromosome of FB21071 using the kDE3 lysogenization kit (Novagen, San Diego, Calif.) to generate the strain BRL01.

Example 2

This example relates to the engineered neuBC pathway, as discussed supra, whose expression was controlled by a T7lac promoter. This experiment describes the introduction of the engineered neuBC pathway into the nanT⁻ *E. coli* strain BRL01 that possesses a lac-controlled T7 RNA polymerase gene.

The neuC and neuB genes of *Neisseria meningitidis* group B, which were introduced into the nanT⁻ *E. coli* strain BRL01, as discussed herein, are sialic acid biosynthetic genes. NeuC is a hydrolyzing epimerase that converts UPD-N-acetylglucosamine (UDP-GlcNAc), a common metabolite in bacteria, to ManNAc. The siaA gene involved in capsule polysaccharide biosynthesis of *Neisseria meningitidis* B codes for N-acylglucosamine-6-phosphate 2-epimerase activity. ManNAc is subsequently condensed with phospenolpyruvate to generate sialic acid through NeuB catalysis, as seen in FIG. 2.

Genomic DNA from *Neisseria meningitidis* ATCC® BAA-335D was used for Polymerase Chain Reaction (PCR). Pfu Turbo® DNA polymerase (Stratagene, La Jolla, Calif.) and the thermocylcer Mastercycler® personal (Eppendorf, Hamburg, Germany) were used for all PCR reactions. The neuB and neuC genes were amplified from *N. meningitidis* MC58 group B genomic DNA by PCR. Primer sequences with engineered restriction sites (listed below in bold) used for cloning of neuC and neuB genes, were used at 0.1 μM for PCR reactions. Cut sites listed were those used to clone the respected gene into vector pKH22. The neuB and neuC primers used for PCR with restriction sites are as follows:

```
neuB (cut site - NdeI/EcoRI)
cgcacatatgcaaaacaacaacgaatttaaaattgg
(forward, SEQ ID NO: 1)

cagcgaattcttattcaatatcagttttttttgatttgagca
(reverse, SEQ ID NO: 2)

neuC (cut site - NheI/EcoRI)
cgcagctagcaaaaggattctttgcattacaggtacc
(forward, SEQ ID No: 3)

cagcgaattcctagtcataactggtggtacatt
(reverse, SEQ ID NO: 4)
```

Touchdown and hotstart PCR were performed for all amplifications, and the thermocycler conditions were as follows: one cycle of 95° C. for 5 min, 15 cycles of 30 s at 95° C., 30 s at 72-57° C. (−1° C. per cycle), and 90 s at 72° C., 15 cycles of 30 s at 95° C., 30 s at 57° C., and 90 s at 72° C., and one cycle of 10 min at 72° C.

PCR products for neuB and neuC were cloned into pCR-Blunt (Invitrogen, Carlsbad, Calif.) following the manufacturer's instructions. Cloned genes were sequenced. An internal EcoRI site in neuB was removed through the Quikchange® site-directed mutagenesis kit (Qiagen, Valencia, Calif.). Genes were subsequently subcloned under the T7lac-promoter of the vector pKH22 to generate the plasmid pBRL22 (pKH22-neuBneuC) using standard molecular cloning techniques. Plasmids have ampicillin resistance markers.

The plasmid pBRL22 was inserted into the nanT⁻ *E. coli* strain BRL01 to form BRL01/pBRL22, where the neuC and neuB genes were overexpressed, using well known and accepted methods in the art.

Although it was hypothesized that the nanT⁻ *E. coli* host BRL01 would not be able to catabolize any sialic acid product because of its inability to uptake sialic acid from the medium, shake-flask experiments involving BRL01/pBRL22 (BRLO1/neuBC) produced low but detectable amounts of sialic acid at 20 mg l⁻¹ with a single feeding of 0.5% GlcNAc as the carbon feeding source.

The low yields were attributed to degradation by endogenous NanA. Therefore, to increase sialic acid yields, the nanA gene in BRL01 was deleted using the lambda Red system to generate the strain BRL02, as discussed in the following Example.

Alternatively, an inactivating mutation in the gene encoding a sialic acid aldolase (such as an inactivating mutation or deletion of the nanA gene) of another microbe (such as another *E. coli* strain) can be used to produce sialic acid, wherein the microbe has a functional sialic acid transporter, as discussed in Examples 5 and 6.

Example 3

This example describes the deletion of the nanA gene of BRL01 using a gene replacement strategy to generate the strain BRL02, and the subsequent introduction of plasmid pBRL22 of Example 2 into BRL02 to form BRL02/pBRL22.

The generation of a nanT⁻ nanA⁻ *E. coli* mutant is important because the nanT gene is involved in sialic acid uptake and the nanA gene is involved in sialic acid degradation. NanT is a sialic acid transporter and is responsible for sialic acid uptake, as noted supra, and NanA is an adolase that cleaves sialic acid into pyruvate and N-acetylmannosamine (ManNAc). The removal of the nanA and nanT genes abolishes sialic acid catabolism, as seen in FIG. 2.

To completely eliminate sialic acid degradation and increase the sialic acid titer, the lambda Red system was used to knockout the nanA gene of BRL01 to generate the nanT⁻ nanA⁻ *E. coli* mutant, BRL02.

Briefly, a cassette encoding tetracycline resistance was amplified from the vector pBR322 (New England Bio Labs, Ipswich, Mass.) using the primers 5'-atggcaacgaatttacgtggcgtaatggctgcactcctgactccttttgatcatgttt gacagcttatcatcgat-3' (SEQ ID No: 5) and 5'-tcacccgcgctcttgcatcaactgctgggccagcgccttcagttctggcatccaatt cttggagtggtgaatccg-3' (SEQ ID No: 6). Primers consisted of 50 nt homology with nanA (underlined) and 25 nt with the tetracycline resistance gene (not underlined). The thermocycler conditions used are identical to those stated above in Example 2. The tetracycline-resistance cassette was gel purified from the PCR reaction and then concentrated by ethanol precipitation. BRL01 transformed with pKD46, which harbors the lambda Red proteins necessary for recombination, were grown in Luria-Bertani (LB) media at 30° C. with shaking, 150 rpm, until an $OD_{600}=0.1$. Expression of the lambda Red genes was then induced with 0.1% arabinose, and the induced cells continued to grow until an $OD_{600}$ of 0.5 was reached. The cells were made electrocompetent and transformed with (100 ng DNA per 50 µl cells) of the tetracycline-resistance cassette. Transformed cells were recovered in LB for 1 hour at 37° C. with shaking and then plated on LB supplemented with kanamycin (50 µg ml) and tetracycline (10 µg ml⁻¹). Transformants were screened for nanA and nanT deletions by PCR.

The plasmid pBRL22 of Example 2 was inserted into the nanT⁻ nanA⁻ *E. coli* strain BRL02 to form BRL02/pBRL22, where the neuC and neuB genes were overexpressed, using well known and accepted methods in the art.

Example 4

This example describes single feeding shake flask experiments involving the BRL02/pBRL22 strain. The BRL02/pBRL22 strain was used to screen carbon source feedstocks including glycerol, maltose, glucose, fructose and GlcNAc, for sialic acid production. For these single feeding experiments, a single initial carbon source at 0.5% was fed to the culture. Cultures were grown for 48 h post induction, and the sialic acid titers were determined.

F1 minimal media consisting of per liter, 6.62 g $K_2HPO_4$, 3.0 g $KH_2PO_4$, 4.0 g $NH_4SO_4$, 170.5 mg $MgSO_4$, and 0.5% filtered-sterilized carbon source, as noted previously, was used for all shake-flask experiments. All media was supplemented with the appropriate antibiotics unless otherwise noted: kanamycin (50 µg ml⁻¹), carbencillin (50 µg ml⁻¹) and tetracycline (10 µg ml⁻¹). All experiments were done in triplicate. Per replicate, a 10 ml starter culture was grown in LB media at 37° C. for 18 h with shaking, 250 rpm. Cells from the starter culture were harvested and diluted into 50 ml of F1 in a 250-ml Erlenmeyer flask. The inoculated cultures were grown at 30° C. with shaking, 150 rpm, and were induced with 0.1 mM isopropyl-β-D-thiogalactopyranoside (IPTG) when their $OD_{600}=0.6$-0.8. The induced cultures were grown for 48, and samples of 1 ml were taken at spaced intervals. Cells were removed from the samples by centrifugation, and the supernatants were boiled for 10 minutes.

Production of sialic acid was confirmed by proton NMR in $D_2O$ using a Bruker 300 MHz instrument. Sialic acid was purified from a cultural broth by removing the cells via centrifugation and then isolating the sialic acid in the supernatant by ion-exchange chromatography as described.

The boiled supernatants, as explained, were quantified for sialic acid activity by the NanA/LDH assay. Briefly, sialic acid concentrations were determined using the sialic acid aldolase-lactate dehydrogenase (NanA/LDH) assay as described. LDH was purchased from Roche (Penzberg, Germany), and NanA was isolated from recombinant *E. coli*. Absorbances were measured in a GENESYS 20 spectrophotometer (Thermo Electron Corporation, Madison, Wis.). The dynamic range of the assay was found to be 0.035 to 0.002 mg ml⁻¹ (0.11 to 0.006 mmol l⁻¹) sialic acid. Reaction conditions consisted of 100 mM Tris buffer (pH 8.0), 0.15 mM NADH, 2.5 µg ml⁻¹ LDH, 5 µg ml⁻¹ NanA, and 0.010-0.030 mg ml⁻¹ of sialic acid. Reactions were carried out with all the above components except NanA at 37° C. for 1 hr. Initial absorbances at 340 nm were then recorded. NanA was then added to the reactions, and the reactions were incubated at 37° C. for 3 h. The final absorbances were measured, and the differences between initial and final absorbance values were fitted against a standard curve to quantify the sialic acid concentration in the samples.

Figure 3:
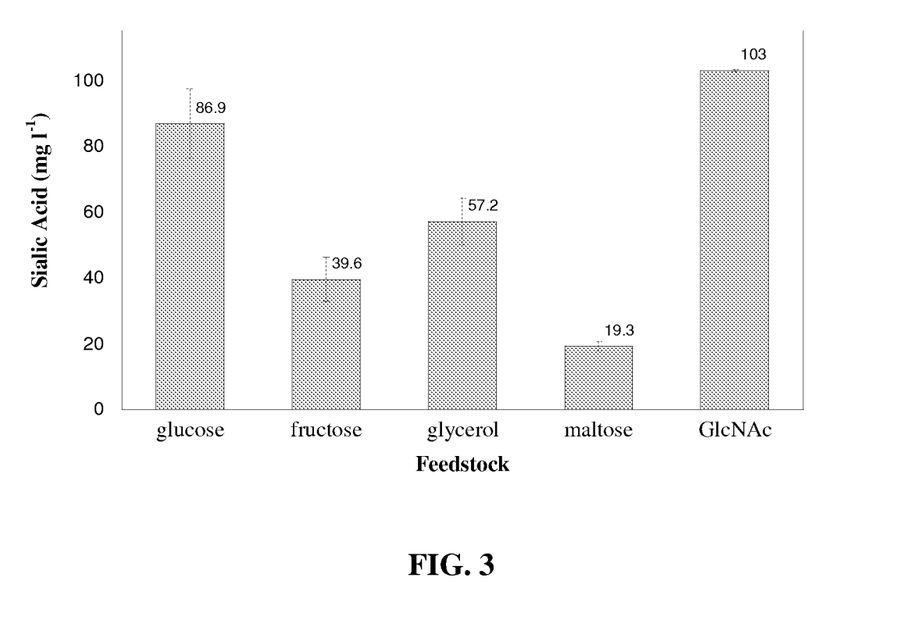
FIG. 3 is a graphical illustration of the effect of a carbon source on sialic acid production in a metabolically engineered E. coli cell, in accordance with an embodiment of the present invention.

The results of these single-feeding experiments are presented in FIG. 3 and are as follows in mg l⁻¹: GlcNAc, 103; glucose, 87; glycerol, 57; fructose, 40; maltose, 19.

The absence of NanA increased the titer 5-fold, as compared with the results noted in Example 2. Not surprisingly, GlcNAc as feedstock produced the highest sialic acid titer; intracellular GlcNAc is converted to UDP-GlcNAc, an important cell wall precursor that is, consequently, the substrate of the neuBC pathway.

The less expensive feedstocks of fructose, glycerol and glucose did not generate as high of a titer as that of GlcNAc, because they first must be incorporated into the GlcNAc biosynthesis pathway, as seen in FIG. 2. GlcNAc biosynthesis in *E. coli* begins with the conversion of fructose into glucosamine by the action of the glucosamine synthase GlmS, which is the key enzyme in GlcNAc metabolism. Thus, Example 7 relates to the co-overexpression of the glmS gene of *E. coli* into the neuBC pathway.

Example 5

This example describes the construction of the reagents required for producing sialic acid in *E. coli* expressing a functional NanT and lacking a functional NanA. The gene encoding the sialic acid transporter, NanT, was amplified from the genomic DNA of XL1Blue *E. coli* by Polymerase Chain Reaction (PCR). Primers used for PCR were 5'-GACGCATATGGGCATCGCCCACCG-3' (SEQ ID No: 7) and 5'-GACGTTAACTTTTGGTTTTGACTAAATCGT-3' (SEQ ID No: 8). The introduced Nde I site is indicated in italics. The amplified nanTPCR product was gel-purified and cloned into pCR-Blunt (Invitrogen) according to the manufacturer's instructions to generate plasmid pBRL50. The internal EcoR I site in nanT was removed using QuikChange to generate plasmid pBRL54. The nanT gene was subsequently cloned into the Nde I and EcoR I sites of pKH22 using standard molecular cloning procedures to generate plasmid pBRL55. The plasmid pBRL55 was digested with Avr II and Xba I, and the Avr II-Xba I nanT fragment was cloned in the forward direction into the Avr II site of pBRL47. This generated plasmid pBRL57, which encodes a polycistronic transcript (5'-3' direction) neuB-neuC-glmS-nanT.

Example 6

This example describes the production of sialic acid in *E. coli* expressing a functional NanT and lacking a functional NanA. BRL02/pBRL47 or BRL02/pBRL57 cells were grown in 50 mL of F1 minimal media supplemented with 50 μg mL$^{-1}$ carbenicillin, 50 μg mL$^{-1}$ kanamycin, 10 μg mL$^{-1}$ tetracycline and 0.5% (w/v) glucose in 250-mL shake flask at 30° C./150 r.p.m. When the optical densities (OD$_{600}$) were 0.7-0.9 AU, cultures were induced with 0.1 mM IPTG and allowed to grow for 72 h. Additional doses of 0.5% (w/v) glucose were added at t=0, 12, 24, 36 and 48 h post induction. Periodically samples were withdrawn and assayed for sialic acid titer by the established NanA/LDH assay. Briefly, cells were removed by centrifugation, and the supernatant was boiled for 10 min and subsequently assayed.

BRL02/pBRL57 cells generated an average sialic acid titer of 315 mg L$^{-1}$ of sialic acid whereas BRL02/pBRL47 cells yielded an average titer of 568 mg L$^{-1}$. In contrast, sialic acid per cell wet weight was greater for BRL02/pBRL57 cells, 515 mg (mg cell wet weight)$^{-1}$, than that of BRL02/pBRL47, 64 mg (mg cell wet weight)$^{-1}$.

Example 7

This example describes the engineering of the glucosamine synthase gene, glmS, of *E. coli* into the neuBC pathway. In particular, this experiment relates to the co-overexpression of the glucosamine synthase gene, glmS, of *E. coli* (amplified by PCR and cloned into pBRL22 to generate plasmid pBRL47) to increase the sialic acid yield from low-cost sugar feedstocks, including glucose and fructose. GlmS is the key enzyme in the biosynthesis of UDP-GlcNAc, the substrate of the neuBC pathway, and glmS overexpression was expected to direct more of the available feedstock sugar into UDP-GlcNAc biosynthesis.

This example incorporates the methods and materials of Example 2 with respect to the amplification and cloning of the neuB and neuC genes to generate the plasmid pBRL47 (pKH22-neuBne CglmS), along with the following: denomic DNA from XL1 Blue *Escherichia coli* (Stratagene, La Jolla, Calif.) was used for PCR. Pfu Turbo® DNA polymerase (Stratagene, La Jolla, Calif.) and the thermocylcer Mastercycler® personal (Eppendorf, Hamburg, Germany) were used for all PCR reactions. The glmS gene was amplified from *E. coli* genomic DNA by PCR. Primer sequences with engineered restriction sites (listed below in bold) used for cloning of the glmS gene, were used at 0.1 μM for PCR reactions. Cut sites listed were those used to clone the respected gene into pKH22. The glmS primers used for PCR with restriction sites are as follows:

```
glmS (cut site - NdeI/EcoRI)
gcgccatatgtgtggaattgttggcgcg
(forward, SEQ ID NO: 9)

gcgcgaattcttactcaaccgtaaccgattttgc
(reverse, SEQ ID NO: 10)
```

Touchdown and hotstart PCR were performed for all amplifications, and the thermocycler conditions were as follows: one cycle of 95° C. for 5 min, 15 cycles of 30 s at 95° C., 30 s at 72-57° C. (−1° C. per cycle), and 90 s at 72° C., 15 cycles of 30 s at 95° C., 30 s at 57° C., and 90 s at 72° C., and one cycle of 10 min at 72° C. Cloned genes were sequenced. Genes were subsequently subcloned under the T7lac-promoter of the vector pKH22 to generate the plasmid pBRL47 (pKH22-neuBne CglmS) using standard molecular cloning techniques. Since the plasmid pBRL47 encodes a neuBne CglmS transcript from a T7lac-promoter, it requires a functional T7 RNA polymerase for transcription. Plasmids have ampicillin resistance markers.

The plasmid pBRL47 was inserted into the nanT nanA *E. coli* strain BRL02 to form BRL02/pBRL47, where the glmS gene was co-overexpressed with the neuC and neuB genes, using well known and accepted methods in the art.

Example 8

All of the materials and methods described in example 4 are incorporated herein, except that only single feeding shake-flask experiments involving the BRL02/pBRL47 strain were performed with fructose as the carbon source.

The results show that single fructose-feeding experiments of BRL02/pBRL47 generated a sialic acid titer of 130 mg l$^{-1}$. Hence, with the addition of glmS to the engineered pathway, a 3-fold increase in sialic acid production, 40 to 130 mg l$^{-1}$, was observed for fructose feeding.

Figure 4:
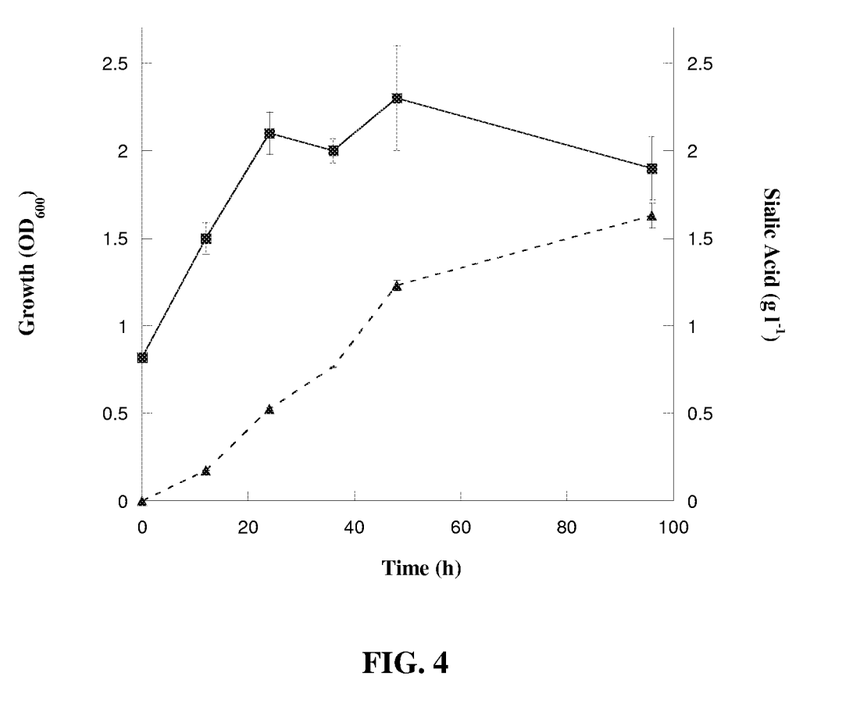
FIG. 4 is a graphical illustration of the optimization of sialic acid production by multiple glucose feedings in accordance with an embodiment of the present invention.

Since fructose feeding produced a significantly lower sialic acid titer than that of glucose in Example 4 (See FIG. 3), the BRL02/pBRL47 strain for sialic acid production was therefore optimized with multiple glucose feedings (even though glucose must be first converted to fructose via gluconeogenesis). As seen in FIG. 4, sialic acid production was optimized to 1.5 grams per liter with glucose feeding under shake-flask conditions. Sialic acid production was measured by the NanA/LDH assay (dotted line). Growth was monitored by measuring the optical density at 600 nm or OD$_{600}$ (solid line). BRL02/neuBCglmS cells were fed 0.5% glucose and ammonium hydroxide (indicated by markers) at 0, 12, 24, 36 and 48 h past induction. Sialic acid production continued to climb during the course of the experiment whereas the growth ceased at 48 h past induction. This figure suggested that the engineered *E. Coli* cells were able to continually produce sialic acid if growth requirements are met.

Example 9

This example describes only multiple feeding shake flask experiments involving the BRL02/pBRL47 strain with glucose as the carbon feeding source. It was expected that a comparable sialic acid titer by single glucose feedings, to that listed in Example 8, would be produced. The same methods and materials were followed and used here as in Example 8, including the shake flask experiments, confirmation of production of sialic acid, and measuring of sialic acid concentration, except as noted in the following paragraph.

Sialic acid production was optimized for BRL02/pBRL47 through multiple feedings of glucose as the carbon source feedstock. Doses of 0.5% of glucose and ammonium hydroxide were added at 0, 12, 24, 36 and 48 h post induction, and the induced BRL02/pBRL47 cells were grown for 98 h (as opposed to 48 h as discussed in Example 4) and the sialic acid titers were determined. The ammonium hydroxide served to maintain the pH 6.9-7.1 and as a nitrogen source.

The results of these examples involving BRL02/pBRL47 (neuBCglmS) cells with the multiple feedings of glucose indicated a maximum or optimized sialic acid titer of 1.5 g l$^{-1}$. Further, this result was obtained with a total of six-feedings of 0.5% glucose (30.0 g of glucose per 1.5 g of sialic acid), as seen in FIG. 4. This result shows that the co-overexpression of glmS with neuBC in BRL02 increased sialic acid production 3-fold from low-cost sugar feedstocks.

This titer was comparable to that obtained from a similar experiment using BRL02/pBRL22(neuBC) with multiple feeding of GlcNAc, which produced a titer of 1.4 g l$^{-1}$.

Example 10

This example involves the production of N-butanoyl sialic acid, an analog of sialic acid. To produce N-butanoyl sialic acid, an N-butanoylglucosamine was first synthesized. Glucosamine hydrochloride (5.0 g, 23 mmol, 1.0 equiv) and triethylamine (16 mL, 115 mmol, 4.8 equiv) were suspended in DMF (48 mL) at room temperature. The reaction mixture was stirred for 30 minutes at which butyric anhydride (4.5 mL, 27 mmoL, 1.2 equiv) was added dropwise. The reaction was stirred for 18 h at room temperature. Ethyl acetate and hexane (800 mL, 1:3 v:v) was added to precipitate the product. The mixture was stirred for 30 minutes, filtered and the solid was repeatedly washed with hexane. The solid was dissolved in methanol (200 mL) filtered and dried under vacuum to afford 5.1 g (20 mmol, 87% yield) of a 1:1 mixture of the α:β anomers of N-butanoyl glucosamine.

N-butanoly sialic acid production from BRL02/pBRL47 was carried out as described in previous shake flask experiments and was optimized by multiple feedings of 0.3% glycerol and either 0.3% N-butanyolglucosamine or N-acetylglucosamine (negative control). Doses of feedstock and ammonium hydroxide were added at 0, 12, 24, 36, and 48 hour post induction, and the induced BRL02/pBRL47 cells were grown for 98 hours. The ammonium hydroxide served to maintain the pH 6.9-7.1 and as a nitrogen source. Combined sialic acid and N-butanoyl sialic acid titers were determined by the NanA/LDH assay. Average combined titer from N-butanoylglucosamine feedings was 67±26 mg/L. Average combined titer from N-acetylglucosamine feedings was 822±23 mg/L.

Example 11

This example describes the construction of an E. coli strain that does not possess functional NanT, NanA and NagA enzymes. The nagA gene in BRL02 was deleted using the Red recombinase system. A chloramphenicol-cassette was amplified from the plasmid pKD3 via Polymerase Chain Reaction (PCR) using primers 5'-ATGTATGCATTAACCCAGGGC-CGGATCTTTACCGGCCACGAATTTCTTGAGTGTAGG CTGGAGCTGCTTC-3' (SEQ ID NO: 11) and 5'-TTAT-TGAGTTACGACCTCGTTACCGTTAAC-GATGGTCTTGGTGATTTTAACATATGAAT ATCCTC-CTTAG (SEQ ID No: 12). Primers consisted of priming sites to pKD3 (italics) and 50 bp homology to nagA. The PCR-amplified cassette was gel-purified, concentrated by ethanol precipitation and suspended in 10 mM Tris buffer, pH 8.0, to a concentration of 40 ng μL$^{-1}$. Approximately 80 ng of the chloramphenicol-cassette was electroporated into BRL02/pKD46 cells, which were prepared according to literature procedure. Chloramphenciol-resistant clones were selected and screened by PCR for replacement at the nagA locus; this generated the strain BRL03. Removal of the chloramphenicol marker in BRL03 was performed by transformation with the plasmid pCP20, which encodes a FLP recombinase. Transformants were selected for ampicillin resistance and not for chloramphenicol resistance. BRL03/pCP20 cells were colony-purified at 43° C. for 18 h. Clones were tested for chloarmphenicol sensitivity and screened by PCR for removal of the chlroamphenicol marker. The removal of the chloramphenicol marker generated the nagA$^-$ strain BRL04.

Example 12

This example describes production of sialic acid from an E. coli strain that does not possess functional NanT, NanA and NagA enzymes. This work demonstrates that down regulating of the nag pathway can be used to optimize sialic titer and per cell per unit time sialic acid productivity. BRL04 cells were transformed with pBRL47, which encodes the neuB-neuC-glmS polycistronic transcript. Sialic acid production experiments were conducted in triplicate. BRL4/pBRL47 cells were grown in 2 mL of F2 minimal media supplemented with 100 μg mL$^{-1}$ ampicillin, 50 μg mL$^{-1}$ kanamycin, 10 μg mL$^{-1}$ tetracycline, and 0.5% (w/v) glucose in a 16×125 mm sterile test-tube. F2 minimal media is identical to F1 minimal media except the former has twice the concentration of phosphate buffer. Cultures were grown for 6 h, induced with 0.5 mM IPTG and grown for 36 h. Sialic acid titers were determined from cell-free supernatants via NanA/LDH assay. BRL04/pBRL47 cells generated an average titer of 0.46 g L-1 sialic acid per liter of culture broth.

What is claimed is:

1. A method of producing sialic acid, comprising the steps of:
providing a genetically engineered microbe, wherein the microbe comprises an inactivating mutation in a first DNA molecule in the microbe that encodes a sialic acid transporter; an inactivating mutation in a second DNA molecule in the microbe the encodes a sialic acid aldolase; and a first enzyme-encoding recombinant DNA molecule in the microbe, wherein the first enzyme-encoding recombinant DNA molecule encodes a uridine diphosphate N-acetylglucosamine 2-epimerase; and a recombinant DNA molecule encoding a glucosamine synthase, wherein the recombinant DNA molecule encoding a glucosamine synthase is a glucosamine synthase gene (glmS), and wherein the overexpression of the glmS gene provides increased uridine diphosphate N-acetylglucosamine levels compared with a wild-type strain; and
culturing the microbe in the presence of a carbon source.

2. The method of claim 1, wherein the microbe is *E. coli*.

3. The method of claim 1, wherein the microbe is capable of transporting sialic acid out of the cell.

4. The method of claim 1, wherein the carbon source is selected from the group consisting of glucose, glycerol, fructose, and N-acetylglucosamine.

5. A method of producing an N-acyl sialic acid analog, comprising the steps of:
providing a genetically engineered microbe, wherein the microbe comprises an inactivating mutation in a first DNA molecule in the microbe that encodes a sialic acid transporter; an inactivating mutation in a second DNA molecule in the microbe that encodes sialic acid aldolase; and a first enzyme-encoding recombinant DNA molecule in the microbe, wherein the first enzyme-encoding recombinant DNA molecule encodes a uridine diphosphate N-acetylglucosamine 2-epimerase; and a recombinant DNA molecule encoding a glucosamine synthase, wherein the recombinant DNA molecule encoding a glucosamine synthase is a glucosamine synthase gene (glmS), and wherein the overexpression of the glmS gene provides increased uridine diphosphate N-acetylglucosamine levels compared with a wild-type strain; and
culturing the microbe in the presence of a reagent such that intracellular uridine diphosphate N-acylglucosamine is generated.

6. A method of producing sialic acid, comprising the steps of:
providing a genetically engineered microbe, wherein the microbe comprises a recombinant DNA molecule encoding a glucosamine synthase, wherein the recombinant DNA molecule encoding a glucosamine synthase is a glucosamine synthase gene (glmS), and wherein the overexpression of the glmS gene provides increased uridine diphosphate N-acetylglucosamine levels compared with a wild-type strain; and culturing the microbe in the presence of a carbon source.

* * * * *